United States Patent [19]
Lehmann

[11] 3,939,187
[45] Feb. 17, 1976

[54] 15α,-SULFONYLOXY-12β-HYDROXYPREGNANES AND PROCESS FOR THE PREPARATION THEREOF

[75] Inventor: Hans-Günter Lehmann, Berlin, Germany

[73] Assignee: Schering Aktiengesellschaft, Berlin & Bergkamen, Germany

[22] Filed: July 2, 1974

[21] Appl. No.: 485,062

[30] Foreign Application Priority Data
July 4, 1973  Germany............................ 2334559

[52] U.S. Cl....... 260/397.45; 260/239.57; 195/51 R
[51] Int. Cl.².................................................. C07J
[58] Field of Search.................. 260/239.57, 397.45;
/Machine Searched Steroids

[56]  References Cited
UNITED STATES PATENTS

| | | | |
|---|---|---|---|
| 3,639,392 | 2/1972 | Fritsch et al.................. | 260/239.57 |
| 3,655,643 | 4/1972 | Lehmann et al.............. | 260/239.57 |

Primary Examiner—Elbert L. Roberts
Attorney, Agent, or Firm—Millen, Raptes & White

[57] ABSTRACT

15α-Sulfonyl-12β-hydroxypregnanes of the formula

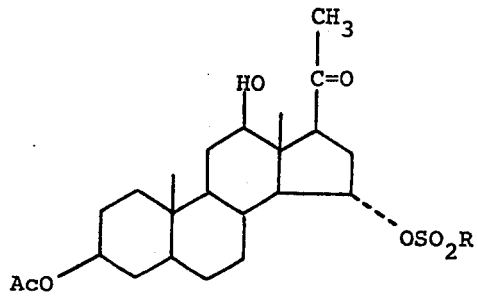

wherein Ac is lower-acyl and R is alkyl, cycloalkyl, aralkyl or aryl, which are useful as intermediates for the production of digoxigenin, are produced by the selective sulfonic acid esterification of the corresponding 12β, 15α-dihydroxy steroid.

10 Claims, No Drawings

15α,-SULFONYLOXY-12β-HYDROXYPREGNANES AND PROCESS FOR THE PREPARATION THEREOF

BACKGROUND OF THE INVENTION

This invention relates to novel 15α-sulfonyloxy-12β-hydroxypregnanes and to a process for their production.

Only the 12β,15α-diesters of 12β,15α-dihydroxy-20-ketopregnanes are known in the literature, such as, for example, the 12β,15α-diacetoxy-4-pregnene-3,20-dione (Helv. 41 [1958] 301; same 46 [1963] 889; or same 48 [1965] 1935), the 3β,12β,15α-triacetoxy-5α-pregnan-20-one, or the 7β,12β, 15α-triacetoxy-5α-pregnane-3,20-dione (J. Chem. Soc. [1972] 2759). Partially esterified 12β,15α-dihydroxy-20-ketopregnanes are not described.

The present invention is directed to the problem of providing intermediates useful in the digoxigenin synthesis by a partial esterification of 12β,15α-dihydroxypregnanes wherein the 15α-hydroxy group is selectively esterified with an ester group which can be split off again under appropriate conditions with the formation of a Δ$^{14}$-double bond.

SUMMARY OF THE INVENTION

According to this invention, a 3β-acyloxy-12β,15α-dihydroxy-20-ketopregnane is selectively esterified with an alkyl-, optionally substituted cycloalkyl-, aralkyl- or aryl-sulfonic acid chloride to produce novel 15α-sulfonyloxy-12β-hydroxypregnanes of the general formula

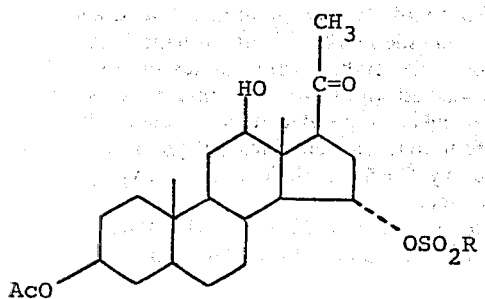

wherein Ac is lower acyl and R is alkyl or optionally substituted cycloalkyl, aralkyl or aryl.

DETAILED DISCUSSION

It was surprising that the esterification with organic sulfonic acid chlorides occurs selectively on the 15α-hydroxy group. In accordance with the di- and triesters known from the literature, it would be expected that the 12β- as well as the 15α-hydroxy group would be esterified.

The term "lower acyl" means the acyl radical of an alkyl, cycloalkyl, lcycloalkylalkyl, carbocyclic aryl or carbocyclic arylalkyl carboxylic acid of up to 8 carbon atoms. Examples are lower-alkanoic, e.g., acetic acid, propionic acid, butyric acid, trimethylacetic acid, valeric acid, cycloalkanoic, e.g., cyclohexylcarboxylic, aryl carboxylic, e.g., benzoic acid, p-toluic acid and arylalkanoic, e.g., phenylacetic.

R of the sulfonic acid ester group can be the organic radical of any organic sulfonic acid, e.g., alkyl of 1–8 carbon atoms, e.g., methyl and ethyl, cycloalkyl of 3–8 carbon atoms, e.g., cyclohexyl and carbocyclic aryl of 6–18 carbon atoms, e.g., phenyl, tolyl, α-naphthyl, β-naphthyl, 2',4',6'-trimethylphenyl, and 2',4',6'-triisopropylphenyl. It will be obvious to those skilled in the art that because the sulfonyloxy group is later split off, R can be the organic radical of any other sulfonic acid.

The process of this invention is conducted by reacting the 12β,15α-dihydroxy steroid in the presence of a tertiary amine with the selected organic sulfonic acid chloride, optionally in a solvent.

Examples of tertiary amines are aliphatic amines, e.g., trimethylamine and tributylamine, and other di-lower-alkylamines, aromatic heterocyclic amines, e.g., pyridine, picolines, lutidine and mixed aromatic-aliphatic amines, e.g., dimethylaniline and other N,N-di-lower-alkyl-amines.

Although in the process of this invention, the chlorides of organic sulfonic acids are ordinarily employed, the corresponding bromides can also be employed.

The reaction of the invention is ordinarily effected at about room temperature without other solvent. However, it is advantageous, especially in case of lower aliphatic R groups or in case of aromatic R groups substituted only to a minor extent, to conduct the reaction at a lower temperature or at a higher dilution. The reaction temperature limits are about −50° C. to about 50° C. If a further solvent for diluting the reaction mixture is desired, any solvent inert with respect to the reactants can be employed, e.g., the halogenated hydrocarbons, including chloroform and methylene chloride, aromatic hydrocarbons, e.g., benzene and toluene, ethers, e.g., diethyl ether and tetrahydrofuran, esters, e.g., ethyl acetate and methyl propionate, and aliphatic hydrocarbons, e.g., hexane and "Decalin" (decahydronaphthalene).

The compounds of this invention are useful as intermediates for the preparation of, for example, digoxigenin. Digoxigenin can be produced, for example, as follows:

12β-Hydroxy-15α-(2',4',6'-trimethylphenylsulfonyloxy)-3β-acetoxy-5β-pregnan-20-one (or other 15α-sulfonyloxy compound of this invention) is acetylated in the 12-position (m.p. 156°–157° C. under decomposition) and, by means of the lead tetraacetate method, an oxygen function is introduced into the 21-position to produce 15α-(2',4',6'-trimethylphenylsulfonyloxy)-3β,12β,21-triacetoxy-5β-pregnan-20-one, m.p. 159°–159.5° C. By splitting off the 15α-sulfonyl ester group with lithium carbonate in dimethylformamide, the corresponding Δ$^{14}$-unsaturated 21-acetoxypregnane is obtained (m.p. 123°–125° C.). After saponification of the 21-acetoxy group, the 21-hydroxy compound, viz., 21-hydroxy-3β,12β-diacetoxy-5β-pregn-14-en-20-one, m.p. 138°–139° C., is reacted with bromoacetyl bromide. The thus-obtained 3β,12β-diacetoxy-21-bromoacetoxy-5β-pregn-14-en-20-one is immediately further processed with trimethyl phosphite to the dimethyl ester of 3β,12β-diacetoxy-20-oxo-5β-pregn-14-en-21-yloxycarbonylmethanephosphoric acid (m.p. 154°–157° C.), which is cyclized by heating in the presence of dimethyl sulfoxide and potassium carbonate to the 3β,12β-diacetoxy-5β-carda-14,20(22)-dienolide (m.p. 170°–171° C.). By treatment with N-chlorosuccinimide in an acidic dioxane/water solution, the 15α-chloro-14β-hydroxy compound is obtained, yielding with tributyltin hydride in the presence of azobisisobutyronitrile, the 14β-hydroxy compound (digoxigenin 3,12-diacetate, m.p. 211.5°–212.5° C.). After saponification with methanolic ammonia, free digoxigenin (m.p. 217°–219° C.) is obtained.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

PREPARATION

The novel starting material for the process of this invention can be produced as follows:

500 ml. of a sterile nutrient solution containing

| 5.0% | glucose | | |
|------|---------|------|---|
| 0.5% | corn steep liquor | 0.05% | potassium chloride |
| 0.2% | sodium nitrate | 0.05% | magnesium sulfate |
| 0.1% | potassium dihydrogen phospate | 0.002% | iron(II) sulfate | is inoculated with a two-week old agar slant of Calonectria decora (ATCC 14 767) and shaken for five days at 30° C.

The thus-obtained subculture serves for inoculating a preliminary fermenter having a capacity of 20 liters, filled with 15 liters of a sterile medium containing

| 5.0% | glucose | 0.025% | potassium chloride |
|------|---------|--------|--------------------|
| 0.25% | corn steep liquor | 0.025% | magnesium sulfate |
| 0.1% | sodium nitrate | 0.001% | iron sulfate |
| 0.05% | potassium dihydrogen phosphate | | |

The subculture is allowed to grow for 72 hours under agitation (220 r.p.m.) and aeration (15 l. of air per minute) at 29° C.

900 ml. of the thus-obtained subculture is transferred into a 20-liter main fermenter containing 14.1 liters of the same medium as the preliminary fermenter. The culture is grown under agitation and aeration for 24 hours at 29° C., combined with a solution of 3.0 g. of 3β-acetoxy-5β-pregnan-20-one in 150 ml. of dimethylformamide, which was filtered under sterile conditions, and the fermentation is continued for another 40 hours.

The fermentation batch is thereafter filtered, the filtrate and the mycelium are extracted with methyl isobutyl ketone. The extracts are combined and concentrated under vacuum. The thus-obtained residue is washed twice with respectively 100 ml. of hexane, and recrystallized from acetone/hexane, thus obtaining 1.73 g. of 12β,15α-dihydroxy-3β-acetoxy-5β-pregnan-20-one, m.p. 228°–230° C.

EXAMPLE 1

2.17 g. of 12β,15α-dihydroxy-3β-acetoxy-5β-pregnan-20-one is dissolved in 22 ml. of absolute pyridine, 2.49 g. of mesitylene-1-sulfochloride is added thereto, and the solution is allowed to stand for 60 hours at room temperature. The mixture is then stirred into ice water, the precipitate is filtered off, washed with water, the residue taken up in methylene chloride, and the solution is dried with sodium sulfate. After concentration, the mixture is purified by chromatography on silica gel. By elution with acetone/hexane, 2.48 g. = 77% of 12β-hydroxy-15α-(2′,4′,6′-trimethylphenylsulfonyloxy)-3β-acetoxy-5β-pregnan-20-one is obtained which, after recrystallization from diisopropyl ether/hexane, melts at 154°–155° C. (decomposition).

EXAMPLE 2

500 mg. of 12β,15α-dihydroxy-3β-acetoxy-5β-pregnan-20-one is dissolved in 5 ml. of absolute pyridine; 500 mg. of p-toluenesulfochloride is added at 0° C., and the mixture is allowed to stand for 30 hours at room temperature. Then, the mixture is poured into ice water, the precipitate is filtered off, washed with water, and, after drying, purified by chromatography on silica gel, thus obtaining 370 mg. = 53% of 12β-hydroxy-15α-tosyloxy-3β-acetoxy-5β-pregnan-20-one, m.p. 138.5°–139° C.

EXAMPLE 3

50 mg. of 12β,15α-dihydroxy-3β-acetoxy-5β-pregnan-20-one is dissolved in 0.5 ml. of absolute pyridine, cooled to −30° C., and 0.017 ml. of mesyl chloride is added thereto. The reaction mixture is left for 10 hours at −30° C. and for one hour at room temperature, diluted with ether, washed with dilute hydrochloric acid and water, and the solvent is evaporated; the product is purified by chromatography in silica gel, thus producing oily 12β-hydroxy-3β-acetoxy-15α-mesyloxy-5β-pregnan-20-one.

NMR spectrum: 0.71 p.p.m. 18-CH$_3$; 0.96 p.p.m. 19-CH$_3$; 2.04 p.p.m. 3-OAc; 2.17 p.p.m. 21-CH$_3$; and 3.50 p.p.m. 15-OSO$_2$CH$_3$.

EXAMPLE 4

50 mg. of 12β,15α-dihydroxy-3β-acetoxy-5β-pregnan-20-one is dissolved in 20 ml. of absolute ether, and then 0.5 ml. of absolute pyridine is added and the mixture is combined with 100 mg. of naphthalene-2-sulfochloride. After 10 hours at room temperature, the mixture is washed with water, the ether phase is dried, and the solvent is evaporated under vacuum. Purification by chromatography on silica gel yields 12β-hydroxy-3β-acetoxy-15α-(naphthalene-2-sulfonyloxy)-5β-pregnan-20-one.

NMR spectrum: 0.73 p.p.m. 18-CH$_3$; 0.96 p.p.m. 19-CH$_3$; 2.04 p.p.m. 3-OAc; 2.18 p.p.m. 21-CH$_3$.

EXAMPLE 5

The procedure analogously to Example 1 is followed, but using 2,4,6-triisopropylbenzene sulfochloride instead of mesitylene sulfochloride, thus obtaining 12β-hydroxy-3β-acetoxy-15α-(2,4,6-triisopropylbenzenesulfonyloxy)-5β-pregnan-20-one.

NMR spectrum: 0.75 p.p.m. 18-CH$_3$; 0.96 p.p.m. 19-CH$_3$; 2.09 p.p.m. 3-OAc; 1.25 p.p.m. iso-prop-CH$_3$.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 15α-sulfonyloxy-12β-hydroxypregnane of the formula

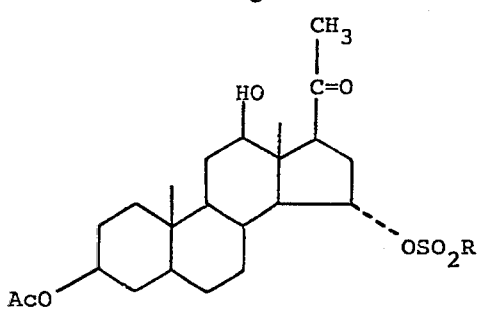

wherein Ac is the acyl radical of an alkyl, cycloalkyl, cycloalkylalkyl, carbocyclic aryl or carbocyclic aralkyl hydrocarbon carboxylic acid of up to 8 carbon atoms and R is alkyl of 1–8 carbon atoms, cycloalkyl of 3–8 carbon atoms or carbocyclic aryl of 6–18 carbon atoms.

2. A compound of claim 1 wherein Ac is acetyl.

3. A compound of claim 1, 12β-hydroxy-15α-(2',4',-6'-trimethylphenylsulfonyloxy)-3β-acetoxy-5β-pregnan-20-one.

4. A compound of claim 1, 12β-hydroxy-15α-tosyloxy-3β-acetoxy-5β-pregnan-20-one.

5. A compound of claim 1, 12β-hydroxy-3β-acetoxy-15α-mesyloxy-5β-pregnan-20-one.

6. A compound of claim 1, 12β-hydroxy-3β-acetoxy-15α-(naphthalene-2-sulfonyloxy)-5β-pregnan-20-one.

7. A compound of claim 1, 12β-hydroxy-3β-acetoxy-15α-(2,4,6-triisopropylbenzenesulfonyloxy)-5β-pregnan-20-one.

8. A process for the production of a 15α-monosulfonyloxy ester of a 12β,15α-dihydroxypregnane of the formula

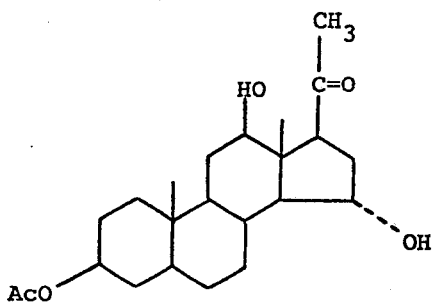

wherein Ac is the acyl radical of a hydrocarbon carboxylic acid of up to 8 carbon atoms, which comprises reacting the 3β-acyloxy-12β,15α-dihydroxy-20-ketopregnane with an organic sulfonic acid chloride, in the presence of the tertiary amine.

9. A process according to claim 8 wherein Ac is acetyl.

10. A process according to claim 1 wherein the reaction is conducted at about room temperature in the presence of pyridine.

* * * * *